United States Patent [19]

Cutler et al.

[11] Patent Number: 5,679,341
[45] Date of Patent: Oct. 21, 1997

[54] BOTCINOL: A NATURAL PRODUCT HERBICIDE

[75] Inventors: Horace G. Cutler, Watkinsville; Stephen R. Parker, Athens, both of Ga.

[73] Assignee: The United States of America as represented by the Secretary of Agriculture, Washington, D.C.

[21] Appl. No.: 499,081

[22] Filed: Jul. 6, 1995

Related U.S. Application Data

[63] Continuation-in-part of Ser. No. 235,432, Apr. 29, 1994, Pat. No. 5,455,221.

[51] Int. Cl.$^6$ ........................................... C12N 1/14
[52] U.S. Cl. .................. 424/93.5; 504/291; 504/271; 435/254.1
[58] Field of Search .............................. 504/291, 271; 435/254.1; 424/93.5

[56] References Cited

PUBLICATIONS

Abstract, Proceedings, Nineteenth Annual Meeting, Plant Growth Regulator Society of America, San Francisco, CA, Jul. 17–20, 1992, "Isolation of a New Biologically–Active Metabolite from *Botrytis cinerea*", H. G. Cutler, et al., published May 1993.

Cutler, Horace G., et al. "Botcinolide: A Biologically Active Natural Product from *Botrytis cinerea*", Biosci. Biotech. Biochem., 11, vol. 57, pp. 1980–1982, Nov. 1993.

Williamson, B. and Duncan, G.H., "Use of cryo–techniques with scanning electron microscopy to study infection of mature red raspberry fruits by *Botrytis cinerea*", New Phytol, 1989, 111, pp. 81–89.

Goodman, B.A., et al., "Non-invasive observation of the development of fungal infection in fruit", Protoplasms, 1992, 166, pp. 107–109.

El–Dei, Ala, et al., "Serological Studies on Some Isolates of *Botrytis cinerea* and other *Botrytis* Species", Phytopathologica Academiae Scientiarum Hungaricae, vol. 20(1–2), 1985, pp. 163–173.

Primary Examiner—Jean C. Witz
Attorney, Agent, or Firm—M. Howard Silverstein; Randall E. Deck; John D. Fado

[57] ABSTRACT

A novel organic compound, designated botcinol, has been isolated which possesses significant phytotoxic activity and which may be used as a biodegradable contact herbicide. The compound is a hydroxylated nonalactone that is esterified with 4-hydroxy-2-decenoic acid, and has the following structure:

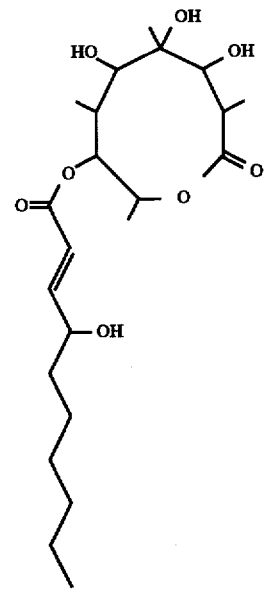

Botcinol is produced by culture of a novel strain of the fungus *Botrytis cinerea*, designated UK 185, and may be subsequently recovered from the culture medium and purified.

7 Claims, No Drawings

BOTCINOL: A NATURAL PRODUCT HERBICIDE

CROSS-REFERENCE TO RELATED APPLICATIONS

This is a continuation-in-part of U.S. patent application Ser. No. 08/235,432, filed Apr., 29, 1994, U.S. Pat. No. 5,155,228.

BACKGROUND OF THE INVENTION

This invention relates to novel hydroxylated nonalactone compounds for use as herbicides. The invention also relates to a novel strain of the fungus *Botrytis cinerea* which produces these compounds.

*Botrytis cinerea* is a common soil fungus which is the causative agent of grey mold rot, one of the most widespread fungal diseases affecting a variety of plants, including agronomically important fruits and vegetables such as lettuce, tomatoes, strawberries, raspberries and grapes.

SUMMARY OF THE INVENTION

We have discovered a novel organic compound possessing significant phytotoxic activity and which may be used as a biodegradable contact herbicide. The compound, which has been given the name botcinol, is a hydroxylated nonalactone that is esterified with 4-hydroxy-2-decenoic acid. Botcinol is produced by culture of a novel strain of the fungus *Botrytis cinerea*, designated UK 185, and may be subsequently recovered from the culture medium and purified.

In accordance with this discovery, it is an object of this invention to provide a novel compound, botcinol, which has phytotoxic activity, and a method for its production.

It is also an object of this invention to provide new compositions including botcinol for control of plant growth.

Another object of the invention is to provide a compound which may be used as a biodegradable contact herbicide.

Yet another objective is to provide a new microorganism which can produce either or both of botcinol or botcinolide.

Other objects and advantages of this invention will become readily apparent from the ensuing description.

DETAILED DESCRIPTION OF THE INVENTION

In our parent U.S. patent application Ser. No. 08/235,432, filed Apr., 29, 1994 (the contents of which are incorporated by reference herein), we disclosed the isolation, identification, and biological activity of botcinolide, a hydroxylated nonalactone esterified with 4-hydroxy-2-octenoic acid and having the structure (I):

The compound was produced by a strain of the phytopathogen *Botrytis cinerea*, designated strain UK 185, found on raspberry fruit (*Rubus ideaus*) growing in a garden in Watkinsville, Ga. Botcinolide significantly inhibited etiolated Wheat coleoptile growth at $10^{-3}$ and $10^{-4}$M by 100 and 82%, respectively, relative to controls. Greenhouse-grown bean, corn, and tobacco plants were affected by treating with botcinolide, and exhibited chlorosis and severe necrosis at $10^{-2}$ and $10^{-3}$M.

Upon further fractionation and analysis of the culture products of *B. cinerea* strain UK 185, yet another biologically active compound was discovered. This new compound, which has been named botcinol, is a hydroxylated nonalactone that is esterified with 4-hydroxy-2-decenoic acid, and has the following structure (II):

Botcinol differs from botcinolide in the length of the side chain; the hydroxylated nonalactone of botcinolide being esterified with the 8-C chain, 4-hydroxy-2-octanoic acid, rather than the 10-C chain of botcinol. However, although the two compounds are structurally related, we have surprisingly discovered that botcinol is significantly more active than botcinolide, possessing herbicidal activity at substantially lower concentrations. Botcinol significantly inhibited wheat coleoptile growth at concentrations as low as $10^{-5}$M, with growth being inhibited at $10^{-3}$, $10^{-4}$, and $10^{-5}$M by 100, 81 and 41%, respectively, relative to controls.

The preferred fungus for the production of both botcinol and botcinolide is a strain of *Botrytis cinerea*, designated UK 185. The strain was classified based upon its characteristic morphology and colonial appearance.

The above-mentioned *Botrytis cinerea* strain UK 185 has been deposited under the Budapest Treaty in the Agricultural Research Service Culture Collection in Peoria, Ill., on Apr. 5, 1995, and has been assigned Deposit No. NRRL 21421.

As described by Gilman (A Manual of Soil Fungi, second edition, Iowa State University Press, Ames, Iowa, 1957, pages 298–300), colonies are diffuse, gray, gray-green, dark olive-green to brown-black, seldom brown or reddish-green. Colonies appear dusty from conidia, may be loose or dense, and are up to 2 mm high.

Morphologically, the conidiophores of the fungus are erect, unbranched or seldom branched, septate, 11–23μ thick, with a black-brown wall which is almost hyalin toward the tip, and with several (three or more) projections at the tip from which the conidia are formed singly on very fine warts. The point of the conidiophore grows between the warts, pressing them back, usually some distance from one another, and they become lateral. The conidia stand so thickly on the projections that thick heads are produced which soon fall off. Conidia are ovate or elliptical to almost globose, finely apiculate at the base, 9–12×6.5–10μ, with an almost hyalin, slightly brown wall.

For the purpose of this invention, any isolate of *Botrytis cinerea* having the identifying characteristics of strain UK 185, including subcultures and variants thereof which retain the ability to produce botcinolide and/or botcinol, are effective. The term variants is defined herein to include transformants and mutants of *Botrytis cinerea* which are capable of producing botcinol and/or botcinolide.

While the mechanism of formation of botcinol and botcinolide has not been established, production of the compounds appears to be concurrent upon culture of *Botrytis cinerea* UK185. For the purposes of this invention, strain UK 185 may be cultivated by any conventional means under any convenient aerobic conditions that are effective to promote growth and botcinol/botcinolide production. While botcinol and botcinolide may be produced by solid-substrate fermentation, optimal production and recovery of the compounds is obtained by liquid-substrate fermentation, particularly with agitation. A variety of well-known liquid and solid media may be used. Preferred liquid media include but are not limited to Mycological broth, Sabouraud dextrose broth, Brain-heart infusion broth, and particularly Potato dextrose broth. The fungus will grow over wide pH and temperature ranges, with acceptable ranges being about 2–7 and 0°–40° C., respectively, with a pH of about 5.5 and a temperature range between about 25°–30° C. being preferred.

Under these suitable cultivation conditions, the subject fungus will produce both botcinol and botcinolide which may be subsequently recovered from the culture medium and purified. Both compounds may be recovered from the culture broth by extraction with a suitable nonpolar solvent, preferably ethyl acetate or a polar/nonpolar solvent such as acetone. Removal of the mycelia and cells prior to such solvent extraction is optional. The solvent phase extract may be separated from the solids and aqueous phase, and the solvent subsequently removed, for example, by evaporation to yield a crude extract of botcinol with botcinolide.

Purification of botcinol and botcinolide from the crude extract and separation from one another may be effected by use of conventional techniques including, but not limited to, countercurrent distribution, column chromatography, high-performance liquid chromatography (HPLC), and thin-layer chromatography. Purification by reverse-phase column chromatography and HPLC is preferred. Without being limited thereto, the details of the preferred purification procedure are described in Example 1.

Commercial formulations containing both botcinol and botcinolide may be prepared directly from crude extracts of the fermentation medium, thereby obviating the need to isolate the compounds in pure form. However, for applications requiring a high degree of specificity or predictability of the intended response, as with botcinolide, it would normally be preferred to prepare the formulations from pure or substantially pure botcinol. A preparation of pure or substantially pure botcinol would exclude other extraneous substances in the natural fungi which might have an adverse effect on the intended activity, or have a toxic effect toward non-target species.

The potency of botcinolide and particularly botcinol dictates that they be applied in conjunction with a suitable solid or liquid inert carrier or vehicle as known in the art. Of particular interest are those which are agronomically acceptable. Alcohols, ketones, esters, and aqueous surfactant mixtures are illustrative of suitable liquid carriers. The compounds may also be formulated with solid inert carriers such as talc, clay or vermiculite, or incorporated into conventional controlled release microparticles or microcapsules. Depending on the substrate, target species, mode of application, and type of response desired, the concentration of active ingredient (the total of botcinol and botcinolide) in the final composition may vary considerably, but typically should be at least about 300 ppm. Factors such as phytotoxicity toward the target plant and tolerance of nontarget species can be used by the skilled artisan in determining the optimum level.

Depending on the target species, concentration of agent, and method of application, botcinol and botcinolide act as herbicides by inhibiting or preventing growth, or inducing mortality of the target plant or seed. The compounds are administered in an amount effective to induce the desired response as predetermined by routine testing. Where the ultimate response is control of plant growth, an "effective amount" or "herbicidally effective amount" is defined to mean those quantities of agent which will result in a significant inhibition or prevention of growth of a test group as compared to an untreated group. Without being limited thereto, it is envisioned that application rates of approximately 50–75 g or more of botcinol per acre will be effective. However, owing to the higher potency of botcinol relative to botcinolide, it is envisioned that lower application rates will also be effective. The actual effective amount will of course vary with the species of plant, stage of development, the nature of the substrate, the type of vehicle or carrier, the period of treatment, and other related factors.

To be effective, botcinol and botcinolide can be directly applied to plants or seeds, or the compound can be applied to the locus of, or the vicinity of, the plant or seed to be controlled. Compositions of the compounds will typically be applied by spraying, although solid formulations may be applied by dusting.

Botcinol and botcinolide are effective in controlling growth of a variety of plants. Without being limited thereto, the compounds are particularly effective against monocotyledonous plants and some dicotyledonous plants, including grasses, tobacco, beans, wheat and corn.

The following examples are intended only to further illustrate the invention and are not intended to limit the scope of the invention which is defined by the claims.

EXAMPLE 1

Production of botcinol and botcinolide.

A strain of *Botrytis cinerea* was isolated from a cultivated raspberry fruit (*Rubus ideaus*) growing in Watkinsville, Ga., and was designated strain UK 185. The taxonomic characteristics of the strain were typical of *Botrytis cinerea*. The biologically pure strain was grown on potato-dextrose agar slants at room temperature for about 14 days and then held at 5° C. for storage prior to use as inoculum.

The potato-dextrose agar slants were flooded with sterile distilled water, and the spores and mycelium suspended therein for use as inoculum. The suspension was transferred to nineteen 2.8 l Fernbach flasks, each containing 500 ml of potato-dextrose broth, and incubated on a rotary shaker at 23° C. for 12 days.

After completion of the fermentation, the culture medium was extracted twice with ethyl acetate equal in volume to the aqueous phase, and the solvent phase separated from the aqueous phase and solid material by decantation. The solvent phase was then dried over anhydrous sodium sulfate, reduced in volume under vacuum at 50° C. to a viscous, gummy residue, and chromatographed on silica gel 60 (70–230 mesh) in an open glass column (5×19 cm) using stepwise elution of 500 ml each of benzene, t-butyl methyl ether, ethyl acetate, acetone and acetonitrile. Approximately 25 μl from each fraction was dried under nitrogen and assayed for biological activity as described below.

Bioassays of the chromatography fractions were conducted by the etiolated wheat coleoptile bioassay of Hancock et al. (1964, J. Exp. Biol., 15:166–176). The bioassay was prepared by sowing wheat seed (*Triticum aestivum* L. cv. Wakeland) on moist vermiculite in plastic trays which were sealed with aluminum foil and kept in the dark at 22°±1° C. for four days. Ten 4 mm sections were cut from each seedling starting exactly 2 mm down from the tip of the plant, and placed in test tubes containing 2 ml of phosphate-citrate buffer at pH 5.6 supplemented with 2% sucrose (Nitsch et al., 1956, Plant Physiol., 31:94–111) and the fraction to be tested for 18 hr (Cutler, Proc. 11th Ann. Meeting Plant Growth Reg. Soc. America, 1984, pp. 1–9). Following this incubation, the coleoptile sections were removed, measured and recorded, and the data were statistically analyzed (Kurtz et al., 1965, Technometrics, 7:95–161).

The fractions that inhibited coleoptile growth, namely the t-butyl methyl ether, ethyl acetate, and acetone fractions were bulked together and reduced in volume under vacuum. This material was chromatographed in a $C_{18}$ reverse-phase glass column (PrepPak 500, Waters Associates; 2×17 cm), using stepwise elution with water and acetonitrile at selected concentrations that ranged from 75:25 of water-acetonitrile (v/v) to neat acetonitrile, yielding pure botcinol and pure botcinolide. An ultraviolet lamp (366 nm) was used to detect the fluorescent and null zones which were individually collected. Again individual fractions were bioassayed by taking 25 μl aliquots, drying them under nitrogen and examining each fraction with etiolated wheat coleoptiles as described hereinabove. Two ranges of fractions were found to exhibit biological activity, the first being tubes 34–38, inclusive, and the second being tubes 39–48, inclusive.

The first range of fractions from tubes 34–38 was subsequently identified as botcinolide as described in U.S. patent application Ser. No. 08/235,432, and in Cutler et al., (1993, Biosci. Biotech. Biochem., 57:1980–1982, the contents of which are incorporated by reference herein). The second range of fractions from tubes 39–48 was identified as botcinol as described in Example 3 hereinbelow.

Botcinolide significantly inhibited wheat coleoptiles at $10^{-3}$ and $10^{-4}$M by 100 and 82%, respectively, relative to controls. No significant inhibition was evident in coleoptiles treated with $10^{-5}$M solutions of botcinolide. In contrast to botcinolide, botcinol exhibited inhibition at much lower concentrations, significantly inhibiting wheat coleoptile growth at $10^{-3}$, $10^{-4}$, and $10^{-5}$M by 100, 81 and 41%, respectively, relative to controls.

Following the reverse phase open column chromatography, the botcinol containing fractions were combined and subjected to semipreparative HPLC on a column (2.2×25 cm, Econosil, Alltech), using 55:45 (v/v) acetonitrile-water and a flow rate of 16 ml/min at room temperature. The UV monitoring of the eluant was at 254 nm. The retention time for botcinol was 6.14 min. Fractions were collected by hand. The acetonitrile was removed by vacuum distillation at 60° C., and the sample then lyophilized to remove water. The final product, a powder, consisted of 120 mg of >98% pure botcinol.

EXAMPLE 2

Phytotoxicity.

Botcinol was tested on greenhouse-grown bean, corn, and tobacco plants in triplicated experiments. Solutions of the metabolite were formulated by dissolving the pure botcinol from Example 1 in acetone and adding water that contained 0.1% Tween 20 to yield final concentrations of $10^{-2}$, $10^{-3}$, $10^{-4}$M in 10% (v/v) acetone. Eight-day-old bean plants (*Phaseolus vulgaris* L. cv., Black Valentine) were sprayed at the first true leaf stage, each pot receiving 1 ml of solution per four plants. Ten-day-old corn plants (*Zea mays* L., cv. Norfolk Market White) were treated by pipetting 100 μl of each test solution into individual leaf sheaths, there being four plants in each pot. Individual six-week-old tobacco plants (*Nicotiana tobacum* L. cv., Hick's) were also treated by spraying with 1 ml of solution. Controls consisted of plants treated with aqueous 10% acetone and 0.1% Tween 20.

No phytotoxic effects were noted on bean plants, although plants treated with $10^{-2}$M solutions had shortened internodes within the first week. However, corn plants exhibited symptoms at 72 hours following treatment and $10^{-2}$M solutions induced necrosis and some stem collapse. At $10^{-3}$ and $10^{-4}$M, there was slight necrosis. By one week, some leaves of the $10^{-2}$M treated plants had become necrotic while others had taken on a russet effect and there were general formative effects. By two weeks, these plants were dwarfed or killed. Six-week old tobacco plants exhibited formative effects in the young expanding leaves at 72 hours following treatment with $10^{-2}$M applications.

EXAMPLE 3

Characterization of Botcinol.

Pure samples of botcinol from example 1 were analyzed to determine the structure of the compound. Thin-layer chromatography was done on silica gel 60, F-254 (E. M. Laboratories) plates developed in toluene-ethyl acetate-formic acid, 5:4:1 (v/v). Botcinol was visualized by spraying the developed plates with anisaldehyde and heating to 100° C. Ultra-violet spectra were obtained with a Hewlett Packard 89532A spectrophotometer. Infrared spectra were obtained with a Nicolet 510P FTIR spectrometer equipped with a 4×beam condenser. Samples were prepared as thin films on KBr windows. Electron impact mass spectra were evaluated by a Hewlett-Packard 5985B mass selective detector, using direct probe sample introduction. Low-resolution positive-ion fast atom bombardment mass spectra (FABMS) were recorded on a VG7070EMF. High-resolution FABMS were evaluated by a Kratos MS50 Triple Analyzer, operated at an accelerating potential of 6 kV. The sample was ionized from a matrix of 3-nitrobenzyl alcohol, using argon. NMR spectra were recorded at 20° C. on a Varian VXR 300A High Field NMR. The $^1$H spectra were gathered at 300 MHz and the $^{13}$C spectra at 75 MHz. The sample consisted of 35 mg of botcinol in $^{12}$CD$_3$OD with TMS as the internal standard. Melting points (uncorrected) were taken on a Kofler block.

The nineteen flasks of *Botrytis cinerea* from Example 1 yielded about 120 mg of botcinol, which was a powder. Thin-layer chromatography gave a distinct deep-blue spot at Rf 0.59–0.66 upon treatment with acidic anisaldehyde and heating. The UV analysis showed end absorption with $\lambda_{max}$ (MeOH) 212. The FTIR spectrum was nearly identical to that of botcinolide with major absorbance peaks at $v_{max}$ 3400 (OH), 2933, 2862, 1711 (C=O), 1654, and 1458 cm$^{-1}$. Direct probe, electron ionization mass spectroscopy gave an incomplete fragmentation pattern, with an apparent M$^+$ at m/z 394 and a major fragment at m/z 226. Neither this, nor the results from chemical ionization mass spectroscopy could be reconciled with the NMR data. FAB hrMS yielded an M$^+$ at m/z 453.2488 and tandem MS-MS confirmed the presence of Na predicting a computer generated formula of C$_{22}$H$_{38}$O$_8$Na. This was consistent with the data obtained from elemental analysis where C and H were shown to be present at 60.5 and 8.7% by weight.

With respect to the NMR spectra, twenty-one signals were observed in the decoupled carbon spectrum corresponding to 5 methyls (14.4, 14.7, 15.0, 17.8 and 18.2 ppm), 5 methylenes (23.6, 26.4, 30.3, 32.9 and 37.5 ppm), 9 methines (39.3, 39.5, 69.3, 71.6, 77.7, 78.5, 79.5, 120.2 and 153.5 ppm of which the fifth and seventh values were weak in the 1D-$^{13}$C spectrum, but were observable in the DEPT as methines), 1 oxygen bearing quaternary (79.9 ppm) and 1 carbonyl carbon (167.7 ppm). A second, poorly relaxed carbonyl was assumed to be present (180 ppm). When compared with the signal pattern of botcinolide (Table 1), substantial similarity between the two structures was inferred. From heteronuclear correlation studies the carbon resonance assigned to an alkene function (signals 19 and 20) each showed couplings to single protons which appeared as double doublets at 6.03 and 6.98 ppm, respectively. The vicinal coupling constant (15.6 Hz) indicated a trans configuration for this double bond. Homonuclear correlation studies confirmed the mutual H-19 and H-20 coupling and showed further strong coupling between the H-20 nucleus and the multiplet at 4.24 ppm. This single proton demonstrated coupling to the oxygen bearing methine signal at 71.6 ppm (signal 14), which in the spectrum of botcinolide was assigned to C-12. In turn, a homonuclear correlation was demonstrated between the 4.24 ppm proton and the proton multiplet at 1.54 ppm attached to the methylene signal at 37.5 ppm (signal 10) that had no corresponding signal in the botcinolide spectrum. Thus, the following partial structure was deduced:

```
      H   H   H
       \ | /
    R₁—C—C—C—R₂
       10  14  19
       C   C   C
      / | 20 | \
     H   OH  H
```

Other than the coupling with H-20, no other coupling was observed between H-19 and other protons, possibly indicating an adjacent quaternary carbon. Consideration of the MS data suggested that the additional two methylene signals in the botcinol NMR spectrum possibly formed part of an extended side chain yielding a structure analogous to botcinolide. The remaining unassigned carbon signals of the botcinol spectrum (2, 3, 4, 5, 11, 12, 13, 15, 16, 17, 18, and 22) very closely matched those of the polyhydroxylated, methyl group substituted nonalactone moiety of botcinolide.

It is understood that the foregoing detailed description is given merely by way of illustration and that modifications and variations may be made therein without departing from the spirit and scope of the invention.

TABLE 1

| Carbon | Botcinolide $\delta^{13}$C(ppm) | Botcinol $\delta^{13}$C(ppm) | Botcinol $\delta^1$H(ppm) | Carbon Signal Number |
|---|---|---|---|---|
| 1 | 180.1(s) | 180.0(s)? | | 22 |
| 2 | 39.7(d) | 3 9.3(d)? | | 11 |
| 3 | 7,7.6(d) | 7 7.7(d)? | | 15 |
| 4 | 79.9(s) | 79.9(s)? | | 18 |
| 5 | 72.4(d) | 79.5(d)? | | 17 |
| 6 | 39.3(d) | 39.5(d)? | | 12 |
| 7 | 78.4(d) | 78.5(d) | 4.34(broad t, 9.63) | 16 |
| 8 | 69.31d) | 69.3(d) | | 13 |
| 9 | 16 7.7(s) | 167.7(s) | | 21 |
| 10 | 120.1(d) | 120.2(d) | 6.03(dd, 1.6, 15.6) | 19 |
| 11 | 153.6(d) | 153.5(d) | 6.98(dd, 4.8, 15.6) | 20 |
| 12 | 71.5(d) | 71.6(d) | 4.24(m) | 14 |
| | | 31.5(t) | 1.54(m) | 10 |
| 13 | 37.2(t) | 32.9(t) | | 9 |
| 14 | 28.6(t) | 30.3(t) | | 8 |
| 15 | 23.6(t) | 26.4(t) | | 7 |
| | | 23.6(t) | | 6 |
| 16 | 14.3(q) | 14.4(q) | | 1 |
| 17 | 17.4(q) | 17.8(q) | | 4 |
| 18 | 14.9(q) | 15.0(q) | | 3 |
| 19 | 14.7(q) | 14.7(q) | | 2 |
| 20 | 18.1(q) | 18.2(q) | | 5 |

| 2 carbonyls | 2 carbonyls |
| 1 O-bearing quaternary | 1 O-bearing quaternary |
| 9 methines (including 2 of a desaturation) 3 methylenes | 9 methines (including 2 of a desaturation) 5 methylenes |
| 5 methyls | 5 methyls |
| 20 carbons | 22 carbons |

"?" denotes weak signal

We claim:

1. A substantially pure compound designated botcinol and having the structure:

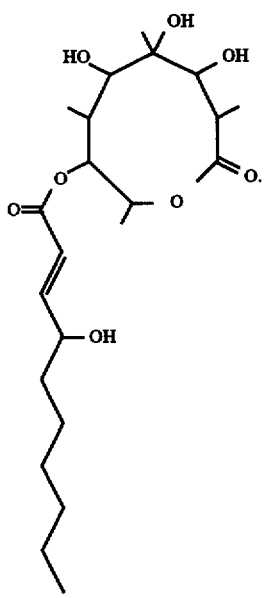

2. A composition comprising a herbicidally effective amount of the compound of claim 1 and an inert carrier.

3. The composition of claim 2 wherein said compound is pure.

4. A method for controlling plant growth comprising providing to the locus of a plant or seed a herbicidally effective amount of the compound of claim 1.

5. The method of claim 4 wherein said compound is pure.

6. The method of claim 4 wherein said plant is a monocot.

7. A biologically pure culture of *Botrytis cinerea* having all the identifying characteristics of *Botrytis cinerea* strain UK 185.

* * * * *